United States Patent
Solly et al.

(10) Patent No.: US 9,027,561 B2
(45) Date of Patent: May 12, 2015

(54) MEDICO-SURGICAL TUBE ASSEMBLIES

(75) Inventors: Caroline Therese Solly, Rye (GB); Neil Adam Tookman, Stanmore (GB)

(73) Assignee: Smiths Group PLC, London (GB)

( * ) Notice: Subject to any disclaimer, the term of this patent is extended or adjusted under 35 U.S.C. 154(b) by 709 days.

(21) Appl. No.: 12/451,001

(22) PCT Filed: May 23, 2008

(86) PCT No.: PCT/GB2008/001743
§ 371 (c)(1),
(2), (4) Date: Oct. 22, 2009

(87) PCT Pub. No.: WO2008/145965
PCT Pub. Date: Dec. 4, 2008

(65) Prior Publication Data
US 2010/0089403 A1    Apr. 15, 2010

(30) Foreign Application Priority Data

Jun. 1, 2007    (GB) .................................. 0710501.8

(51) Int. Cl.
*A61M 16/04*    (2006.01)
(52) U.S. Cl.
CPC ......... *A61M 16/047* (2013.01); *A61M 16/0465* (2013.01); *A61M 16/0497* (2013.01)
(58) Field of Classification Search
CPC ....................... A61M 16/04–16/0497
USPC .......................... 128/200.24, 200.26, 204.18, 128/207.14–207.17
See application file for complete search history.

(56) References Cited

U.S. PATENT DOCUMENTS

| | | | | |
|---|---|---|---|---|
| 3,973,569 | A * | 8/1976 | Sheridan et al. | 128/207.15 |
| 4,009,720 | A * | 3/1977 | Crandall | 128/207.15 |
| 4,235,229 | A * | 11/1980 | Ranford et al. | 128/207.17 |
| 4,649,913 | A * | 3/1987 | Watson | 128/207.14 |
| 4,877,025 | A * | 10/1989 | Hanson | 128/204.16 |
| 5,123,410 | A * | 6/1992 | Greene et al. | 128/207.17 |
| 5,782,236 | A * | 7/1998 | Ess | 128/207.17 |
| 6,105,577 | A * | 8/2000 | Varner | 128/207.17 |
| 6,615,832 | B1 * | 9/2003 | Chen | 128/206.26 |
| 7,506,647 | B2 * | 3/2009 | Worthington | 128/207.14 |
| 2002/0139372 | A1 * | 10/2002 | Shikani | 128/207.17 |

FOREIGN PATENT DOCUMENTS

JP    61-041470    2/1986

* cited by examiner

*Primary Examiner* — Valerie L Skorupa
(74) *Attorney, Agent, or Firm* — Louis Woo

(57) ABSTRACT

A tracheostomy tube assembly has a flange arrangement (2) movable along the shaft (1) of the assembly and lockable at different positions. The flange arrangement has a gel-filled member (22) with a flexible conformable surface (26) providing substantially the entire surface contacting the skin. The flange has aperture (28) through which a tape can be extended for use in securing the assembly with the patient's neck. The gel-filled member (122) may be provided separately for use on existing tube assemblies.

1 Claim, 3 Drawing Sheets

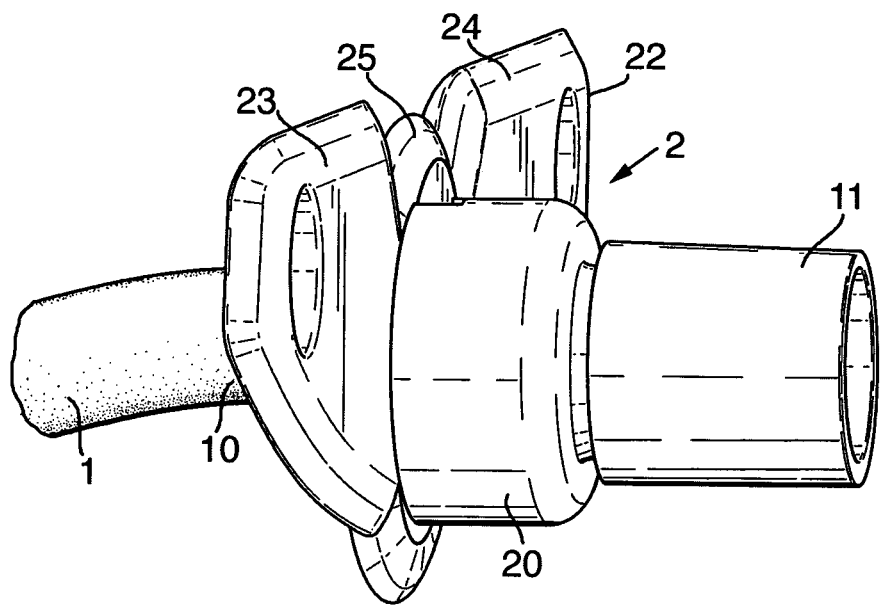
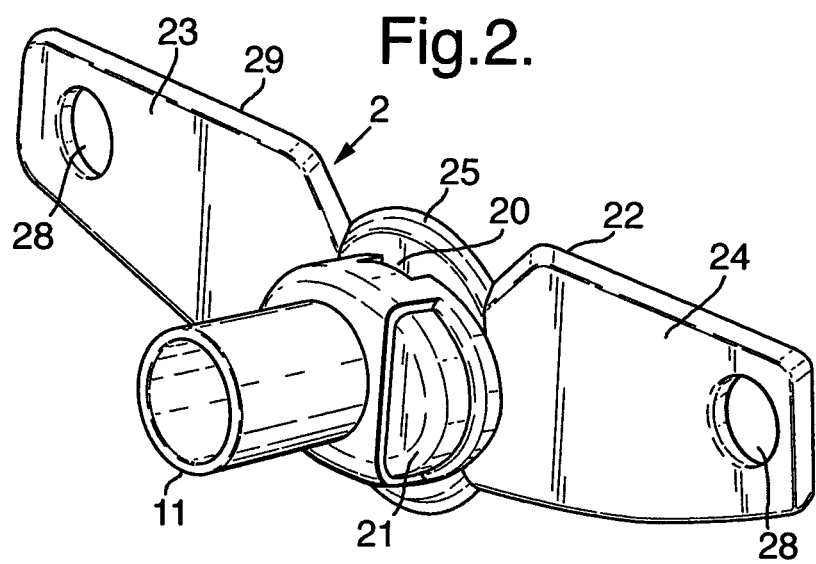

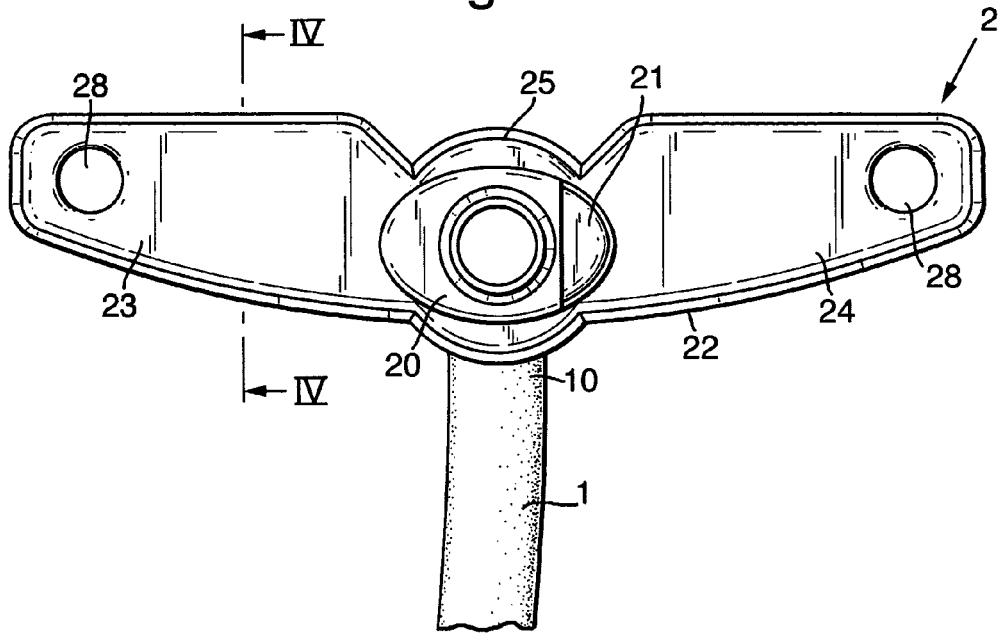
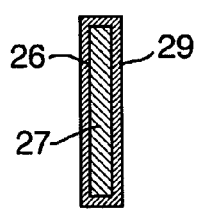
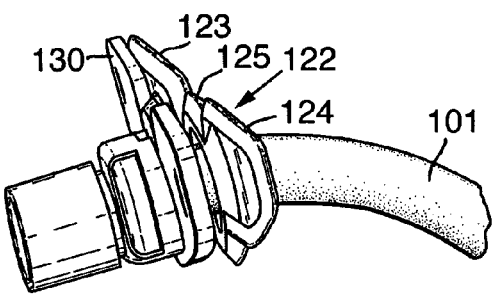
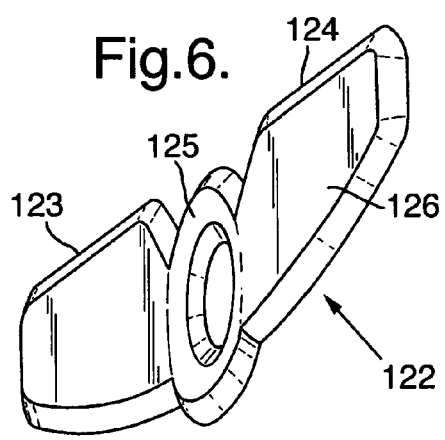

MEDICO-SURGICAL TUBE ASSEMBLIES

This invention relates to medico-surgical tube assemblies of the kind including a tubular shaft arranged to extend within the body via an opening and a flange arrangement mounted with the shaft and having a surface adapted to contact the external skin surface of the patient.

Medico-surgical tubes, such as tracheostomy tubes, are commonly provided with a flange to secure the tube to the patient's body. In the case of a tracheostomy tube, the flange is positioned close to the surface of the neck where the tube enters the tracheostomy, a tape is threaded through openings in the flange and fastened around the neck. Tracheostomy tubes may be worn for prolonged periods and the contact of the flange on the delicate skin of the neck around the tracheostomy can cause discomfort and irritation. This is a particular problem with freshly formed stomas.

There are other medico-surgical tubes with flanges having a similar problem.

It is an object of the present invention to provide an alternative medico-surgical tube assembly.

According to one aspect of the present invention there is provided a medico-surgical tube assembly of the above-specified kind, characterised in that the skin-contacting surface is provided by a gel-filled member arranged to contact the skin.

The gel-filled member preferably provides substantially the entire surface contacting the skin. The flange arrangement may include an outer flange, the gel-filled member being located between the outer flange and the skin surface. The gel-filled member may be provided as a separate component from the outer flange. Alternatively, the flange arrangement may be provided by a flange containing a gel substance and having a conformable skin-facing surface. The conformable skin-facing surface may be provided by a thin wall of a flexible plastics material. The flange may include a plurality of gel-filled members. The flange arrangement may include an outer flange, a gel-filled member having a surface adapted to contact the patient's skin surface and a gas-filled member located between the outer flange and the gel-filled member. The gas-filled member is preferably inflatable.

According to another aspect of the present invention there is provided a tracheostomy tube assembly including a tubular shaft arranged to extend within the trachea via a tracheostomy and a flange arrangement mounted with the shaft and extending laterally on opposite sides of the shaft, the flange arrangement having a surface adapted to contact the external skin surface of the neck of the patient and provided with apertures to receive a tape used to secure the assembly with the patient's neck, the skin-contacting surface being provided by a gel-filled member arranged to contact the skin.

The gel may be a silicone material or hydrogel. The flange arrangement may be movable along the shaft.

According to a further aspect of the present invention there is provided a gel-filled component for a tube assembly of the kind including a tubular shaft arranged to extend within the body via an opening and a flange mounted with the shaft and having a skin-facing surface, characterised in that the gel-filled component is slidable along the shaft to be positioned between the skin-facing surface of the flange and the patient's skin, and that the gel-filled component provides a conformable surface arranged to contact the patient's skin in use.

Several examples of different forms of tracheostomy tube assembly according to the present invention will now be described, by way of example, with reference to the accompanying drawings, in which:

FIG. 1 is a side elevation view of the machine end of a first form of tube assembly;

FIG. 2 is a perspective view of machine end of the assembly of FIG. 1;

FIG. 3 is an end view of assembly at the machine end;

FIG. 4 is a cross-section view across the flange of the assembly along the line IV-IV of FIG. 3;

FIG. 5 is a side elevation view of the machine end of an alternative assembly where the flange assembly includes a plastic flange and a separate gel-filled flange located between the plastic flange and the neck surface;

FIG. 6 is a perspective view of the gel-filled flange of the arrangement of FIG. 5;

Figure 7:
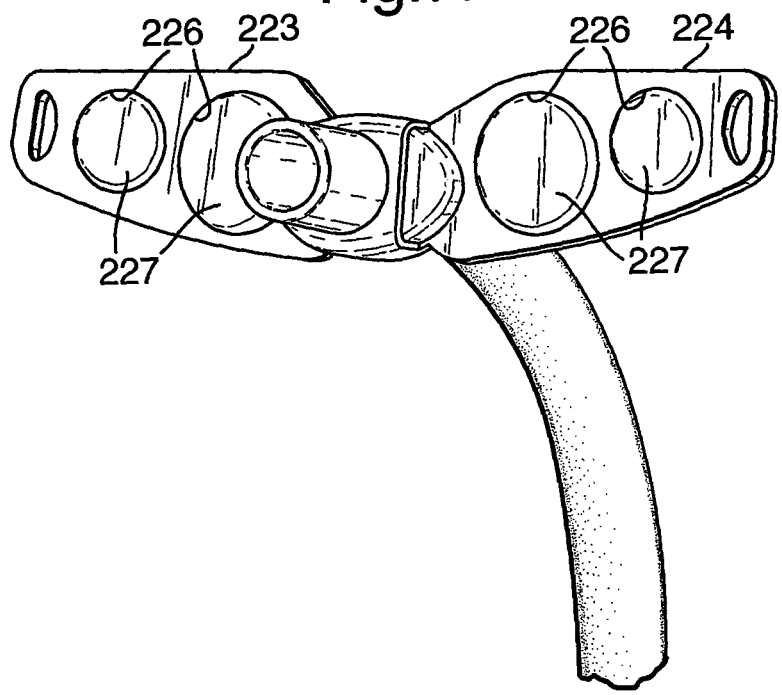
FIG. 7 is a perspective view of a third tracheostomy tube assembly.

With reference first to FIGS. 1 to 4 there is shown the machine end of a first form of tracheostomy tube assembly comprising a tubular shaft 1 and a flange arrangement 2 mounted on the shaft. The shaft 1 is entirely conventional, being extruded or moulded of a plastics material and being curved along its length to an appropriate anatomical shape. The patient end of the shaft (not shown) may be provided with a conventional inflatable sealing cuff or it may be plain. The machine end 10 of the shaft 1 is terminated by a luer-tapered coupling 11 of conventional kind bonded with the end of the shaft. The flange assembly 2 is movable along the shaft 1 and is lockable in any desired position, although alternative embodiments could have a flange that is fixed in position relative to the shaft. The flange assembly 2 of the present embodiment includes a rear locking clamp 20, preferably of the kind described in WO08/003929. The clamp 20 includes a rotatable arm 21, which is swung down to the position shown in FIGS. 2 and 3 to cause the clamp to grip the outside of the shaft 1. The clamp 20 is mounted on the rear face of a forward component 22 providing two elongate wings 23 and 24 extending outwardly from a central disc 25. The wing component 22 includes an outer wall 26 of a relatively thin, flexible plastics material such as polyurethane or urethane enclosing a filling of a gel material 27, as most clearly shown in FIG. 4. The gel material 27 may be of any conventional medical grade gel, such as ComfortGel sold by Respironics, a silicone or hydrogel, or a gel of the kind described in U.S. Pat. No. 6,631,718. The thin nature of the wall 26 and the gel filling 27 make the flange wings 23 and 24 highly flexible, conformable and soft. The flange wings 23 and 24 each have an aperture 28 towards their outer ends through which is threaded a tape or the like used to secure the tube assembly in position about the neck of the patient. In use, the skin around the stoma is contacted by the forward surface 29 of the wing component 22, the soft nature of the flange ensuring that it conforms closely to the anatomy, thereby distributing pressure evenly, producing a good fit and ensuring excellent patient comfort.

Instead of making the flange itself of a gel-filled material, the present invention enables conventional tracheostomy tubes to be modified in the manner shown in FIGS. 5 and 6. In this embodiment, a gel-filled component 122 with a central disc 125 and two wings 123 and 124 is provided as a separate component, which can be slipped onto the shaft 101 and slid into position on the forward side of a conventional solid plastics outer flange 130. In this way it acts as a conformable pillow between the flange and the patient's skin and provides a conformable skin-contacting surface 126.

In both these arrangements, the entire contact with the patient's skin surface is by a gel-filled component.

FIG. 7 shows a third embodiment where a tracheostomy flange 222 is of a solid plastics material but includes within it gel-filled regions adapted to contact the skin surface. As shown, in this example, each wing 223 and 224 includes two circular apertures 226 formed through it and each containing a circular insert 227 in the form of a pillow having a flexible plastics wall enclosing a gel filling. The pillows 227 each project slightly beyond the forward and rear surfaces of the wings 223 and 224 so that the major contact of the flange with the skin is via the gel-filled pillows.

Figure 8:
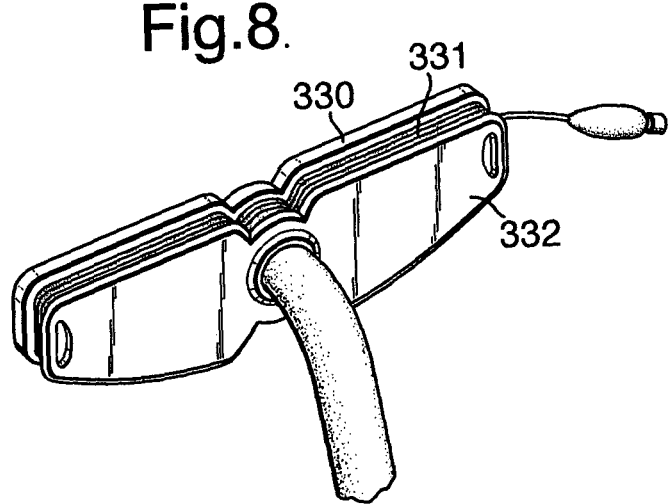
FIG. 8 is a perspective view of a fourth tracheostomy tube assembly.

The fourth arrangement shown in FIG. 8 is similar to the arrangement of FIGS. 5 and 6 except that the outer plastics flange 330 includes an inflatable air sack 331 on its forward facing surface and a gel-filled flange 332 on the forward surface of the air sack. The air sack 331 can be inflated or deflated as desired to provide the best possible fit to the patient's anatomy. The inflatable air sack 331 may be similar to the arrangement described in U.S. Pat. No. 4,649,913.

The invention claimed is:

1. Apparatus, comprising a gel-filled component slidable onto a tubular shaft of a tube assembly arranged to extend within body of a patient via an opening and a flange with two elongate wings mounted with the shaft and having a skin-facing surface, the wings of the flange having apertures to enable a tape to secure the tube assembly about a neck of the patient, the gel-filled component being slidable along the shaft relative to the flange to be positioned between the skin-facing surface of the two elongate wings of the flange and skin of the patient, the gel-filled component providing a conformable surface arranged to contact the skin of the patient in use.

* * * * *